US00PP11034P

United States Patent [19]

Andersen et al.

[11] Patent Number: Plant 11,034

[45] Date of Patent: Aug. 17, 1999

[54] SWEET CHERRY CULTIVAR NAMED 'HARTLAND'

[75] Inventors: Robert L. Andersen; Susan K. Brown, both of Geneva; Roger D. Way, Stanley; Kenneth G. Livermore, Geneva; David E. Terry, Ovid, all of N.Y.

[73] Assignee: Cornell Research Foundation, Inc., Ithaca, N.Y.

[21] Appl. No.: 08/835,640

[22] Filed: Apr. 10, 1997

Related U.S. Application Data

[63] Continuation of application No. 08/652,991, May 24, 1996, abandoned, which is a continuation of application No. 08/526,863, Sep. 13, 1995, abandoned, which is a continuation of application No. 08/278,128, Jul. 21, 1994, abandoned, which is a continuation of application No. 08/135,126, Oct. 12, 1993, abandoned, which is a continuation of application No. 07/971,724, Nov. 4, 1992, abandoned.

[51] Int. Cl.[6] ..... A01H 5/00

[52] U.S. Cl. ..... Plt./181

[58] Field of Search ..... Plt./37, 181

*Primary Examiner*—Howard J. Locker

[57] ABSTRACT

A new distinct cultivar of sweet cherry (*Prunus avium*) which is exceptional in combining 1) ability to bear consistently large crops, 2) having wide pollenizer utility, and 3) having a uniquely spreading moderately drooping tree form. The cultivar is named 'Hartland' and was tested as NY 3308.

2 Drawing Sheets

CROSS-REFERENCE TO RELATED APPLICATIONS

This application is a continuation of Application Ser. No. 08/652,991, filed May 24, 1996, now abandoned, which is a continuation of Application Ser. No. 08/526,863, filed Sep. 13, 1995, now abandoned, which is a continuation of Application Ser. No. 08/278,128, filed Jul. 21, 1994, now abandoned, which is a continuation of Application Ser. No. 08/135,126, filed Oct. 12, 1993, now abandoned, which is a continuation of Application Ser. No. 08/971,724, filed Nov. 4, 1992, now abandoned.

BACKGROUND OF THE INVENTION

In 1951 twenty-seven open-pollinated seeds from unknown male parent source were gathered from a Windsor cherry tree growing on the New York State Agricultural Experiment Station (Station). This seed was given cold treatment to satisfy its stratification requirement along with other seeds derived from our research. In 1952 it was planted in a research field designated as Crittenden 29, Row 3, Tree 45 (C29R3T45). A single tree resulted. This single tree from one of the 27 original open-pollinated seeds was the tree from which the cultivar of the invention originated. When the tree resulting from this seed bore fruit we observed it for two seasons and in 1958 we selected it because it had a uniquely spreading tree and a heavy crop of attractive fruit. It was designated NY 3308 and grafted in 1959 utilizing the nursery T-budding grafting technique. These grafts produced trees to be used for more tests of this selection's merit. Grafted trees that resulted were planted in 1961 in a Station field designated as Loomis 34, Row 9, Tree 31. Further grafted trees resulted from 1965 T-budding utilizing propagating wood taken from the L34R9T31. These were harvested in 1966 and stored in the Station tree storage facilities until the spring of 1967 when they were planted in Station research fields which are designated Denton, Row 5, Tree 8 and Lucey, Row 3, Tree 30. Subsequently this process of clonal propagation to perpetuate the NY 3308 selection has been repeated twice more utilizing L34R9T31 as a source plant. This gave rise to the currently living trees at the Station which are designated as Lucey 50, Row 3, Trees 2 through 7 and Crittenden 29, Row 7, Tree 50 and Crittenden 29, Row 8, Trees 1, 2 and 4. These trees have been observed by different members of the team of inventors in different seasons. Fruiting trees have had research observations taken about their performance on a regular basis. Other trees from our nursery propagation were distributed during the 1980's to other public research agencies in the USA, Canada, and France. Similarly trees or propagating budwood to make trees has been distributed to private orchardists-cooperators for the purpose of testing utilizing a restrictive distribution agreement.

DESCRIPTION OF RELATED ART

In all test plantings, trees of NY 3308 (now being named and released as 'Hartland') bore consistently heavy fruit crops as judged by experienced researchers and cherry orchardists. Some of these trees were tested during blossom time for pollenizer effectiveness and were found to belong to the pollenizer group designated as Group VI (S3S6). This is an important finding since this group is not widely represented in commercial sweet cherry cultivar plantings throughout the world. Hence, 'Hartland' is uniquely well suited to be employed as a pollenizer in commercial orchards. Trees of 'Hartland' have been precocious in setting a fruit crop earlier in their life time than many other sorts that we have had under test. 'Hartland' trees also had a unique, spreading tree form and, while of questionable value to orchardists, its slightly pendulous habit and leaves which always show more mid-vein, upward folding in hot weather, are also distinctive traits. Trees of 'Hartland' are vigorous and their flowering spurs are retained in fruiting condition longer than many cultivars which have the same combination of tree growth habit and fruiting characteristics as this invention.

There follows comparison of four traits of 29 Sweet cherry cultivars and selections including 'Hartland' (NY3308) originally published by Brown et al, *HortScience* 23:902–904 (1988).

For this study, a precise method for measuring both sweet cherry flesh and skin strength was required. The Instron Universal Testing Machine was chosen because it has been used to measure effectively components of firmness in fruit crops. The objective of the present study was to evaluate both total firmness (skin and underlying flesh) and flesh firmness of sweet cherry germ plasm by means of the Instron puncture test. We wanted to determine how effectively differences in these two components of firmness could be detected within and between sweet cherry selections and cultivars. To provide a representative sample of material being used in breeding, standard cultivars were included in this study, along with several promising New York selections that were obtained by open pollination or from hybridizations between commercially important cultivars (Table 1). The object was to assess the variability present within the breeding program for these components of firmness. The material being tested would also provide an objective assessment of how New york breeding selections compare with standard commercially grown cultivars.

Fruit and plant characteristics thought to be indicative of fruit maturity were also measured. These included fruit weight, the dimensions of the fruit (length, breadth, and width), soluble solids content (SSC) and fruit removal force. Correlations between these characteristics and fruit firmness were examined to determine if the firmness of the sample was related to the relative stage of maturity or to any of the other measured characteristics.

Fruit samples were obtained from trees grown in an orchard at the New York State Agricultural Experiment Station at Geneva. Since the optimum harvest date of sweet cherries is difficult to assess, previous performance records were used in an effort to ensure that selection and cultivars were harvested at the same relative stage of fruit maturity. The fruit size and color at harvest met commercial standards for the fresh market. Fruit were harvested at the red-mahogany stage as determined by reference to the cherry color comparator #6 (Tech West Enterprises, Ltd., Vancouver, B.C.).

TABLE 1

Parentage of the Cultivars and New York Selections Evaluated

| Cultivar of Selection | Type[z] | Parentage |
|---|---|---|
| Bada | W | Unknown seedling X Ord |
| Bing | B | Republican open pollinated |
| Cavalier | B | Unknown |
| Early Rivers | B | Early Purple open pollinated |
| Emperor Francis | W | Unknown |
| Hedelfingen | B | Unknown |
| Hudson | B | Oswego X Giant |
| May Duke | D | Unknown (but sweet X tart cherry) |
| Merton Bounty | B | Elton X Schrecken |
| Merton Reward | B | Emperor Francis X Bedford Prolific |
| Moreau | B | Unknown |
| NY 1507 | B | Schmidt X Bing |
| NY 3308 | B | Windsor open pollinated |
| NY 3801 | W | Bing X NY 1495 [Emperor Francis X Gil Peck] |
| NY 5929 | B | Kristin [E. Francis X Gil Peck] X S. Hardy. Giant |
| NY 6476 | B | Van X Vic [Bing X Schmidt] |
| NY 7679 | W | Pr. 1–638 X NY 5656 [E. Francis X Napoleon] |
| NY 9801 | B | Schneider open pollinated |
| NY 11390 | B | Chinook [Bing X Gil Peck] open pollinated |
| Rainier | W | Bing X Van |

TABLE 1-continued

Parentage of the Cultivars and New York Selections Evaluated

| Cultivar of Selection | Type[z] | Parentage |
|---|---|---|
| Sam | B | (Windsor open pollinated seedling) open pollinated |
| Schmidt | B | F. Schwarze Knopelkirsche open pollinated |
| Starkrimson | B | Stella X Garden Bing |
| Stella | B | Lambert [Napoleon X Black Heart] X J.I.2420 |
| Ulster | B | Schmidt X Lambert |
| Van | B | Empress Eugenie open pollinated |
| Victor | W | Windsor open pollinated |
| Viva | B | Ukendt X Victor |
| Windsor | B | Unknown |

[z]B = dark sweet cherry, W = white fleshed sweet cherry, D = duke

One random sample of 30 fruit was harvested from single trees of each cultivar or selection. Individual fruits were weighed and the length (base to apex), breadth (i.e. cheek), and width (i.e. suture) of each fruit was measured in millimeters. Fruit were then placed in refrigerated storage 4.5° C. for several hours before Instron testing to eliminate any variation due to temperature.

Fruit firmness was measured with the Instron Universal Testing Machine (Instron Corp., Canton, Mass.). Full scale load was set at 5. The crosshead speed was 5 $cm \cdot min^{-1}$, and chart speed 10 $cm \cdot min^{-1}$. Intact fruit was positioned so that the stem was in the horizontal plane. The skin of the fruit was punctured with a #41 drill blank (probe diameter 2.4 mm) on the area of the cheek to the right of the suture and the maximum force measured in newtons. Skin was removed from an adjacent area of the cheek on the opposite side of the suture and the same procedure was repeated to determine flesh firmness.

Fruit removal force (FRF), or the force required to remove the fruit from its stem, was determined using a Hunter mechanical Force Gauge (Ametek, Inc., Hatfield, Pa.). Fruit SSC was measured on the expressed juice of individual fruit with a hand-held refractometer.

All characteristics were analyzed by a one way analysis of variance (ANOVA) with cultivar being the variable. Means were separated by the method of LSD at the 5% level.

The ANOVA established significant cultivar effects for all fruit quality characteristics. The means for flesh and total puncture values, SSC, and fruit removal force are presented in Table 2. The cultivars and selections are arranged in order of their flesh puncture values, from the firmest (the highest value) to the softest.

Although fruit color is used commercially to gauge maturity, fruit removal force, fruit size, weight, and SSC are other important characteristics that can be used to assess fruit maturity. It was initially thought that some of the differences in firmness might be attributed to differences in maturity, but found that the correlation between SSC and the flesh puncture value was not significant. The correlations between the flesh and total puncture values and FRF also were not significant (Table 3). This is evident when comparing firmness values of selections and cultivars with the same relative FRF, such as 'Van' and 'Hedelfingen' (Table 2).

TABLE 2

Means for Instron Puncture Values of Flesh Firmness and Total Firmness (skin and flesh combined), Soluble Solids Content (SSC), and Fruit Removal Force (FRF) of Sweet Cherry Cultivars and Selections

| Cultivar or Selection | Flesh (N) | Total (N) | SSC (% Brix) | FRF (g) |
|---|---|---|---|---|
| Moreau | 1.28 a[z] | 3.73 ef | 14.2 mn | 609 bc |
| NY 6476 | 1.21 ab | 4.17 bcd | 16.5 fgh | 422 f–j |
| Emperor Francis | 1.13 b | 4.44 ab | 17.4 cde | 550 d |
| Ulster | 0.97 c | 4.22 bc | 19.1 ab | 466 ef |
| NY 3801 | 0.97 c | 3.20 ijk | 13.7 n | 632 ab |
| Rainier | 0.95 c | 3.91 de | 17.0 d–g | 435 f–i |
| NY 9801 | 0.80 d | 3.77 ef | 18.9 ab | 419 g–k |
| NY 1507 | 0.79 d | 4.66 a | 19.4 a | 391 ijk |
| NY 5929 | 0.78 d | 3.18 ijk | 19.4 a | 342 lm |
| NY 3308 | 0.78 d | 3.21 ij | 15.9 hij | 489 c |
| Hudson | 0.77 de | 3.90 de | 17.7 cd | 569 cd |
| Bing | 0.76 de | 3.38 ghi | 19.1 ab | 326 m |
| Schmidt | 0.76 de | 3.42 ghi | 18.6 b | 397 h–k |
| Cavalier | 0.74 def | 3.93 cde | 15.5 jk | 465 ef |
| Van | 0.73 def | 2.78 mn | 18.9 ab | 436 fgh |
| Starkrimson | 0.72 d–g | 3.41 ghi | 14.0 n | 611 bc |
| NY 11390 | 0.69 c–h | 3.05 j–m | 19.4 a | 554 d |
| Sam | 0.66 f–j | 3.35 hi | 14.9 klm | 658 a |
| Bada | 0.63 g–j | 3.56 fgh | 17.3 cde | 430 f–j |
| NY 7679 | 0.62 hij | 3.20 ijk | 17.1 def | 270 n |
| Windsor | 0.58 ijk | 2.92 k–n | 15.8 ij | 419 g–k |
| Stella | 0.55 jkl | 3.21 ij | 16.0 hij | 573 cd |
| Victor | 0.54 jkl | 3.67 efg | 15.0 kl | 498 e |
| Viva | 0.51 klm | 3.13 i–l | 16.9 efg | 386 jkl |
| Hedelfingen | 0.49 klm | 2.88 lmn | 14.8 lm | 412 h–k |
| Merton Reward | 0.48 lm | 3.03 j–m | 16.4 ghi | 380 kl |
| May Duke | 0.43 mn | 2.67 no | 17.9 c | 401 c |
| Early Rivers | 0.42 mn | 2.34 p | 13.9 n | 460 efg |
| Merton Bounty | 0.39 n | 2.39 op | 17.0 d–g | 426 f–j |

[z]Means within a column separated by LSD, P = 5%. Each number is the mean value for 30 fruit.

The correlations presented are across all genotypes, but correlations within genotypes followed the same pattern. The lack of any large, significant correlations between firmness and the characteristics commonly used to indicate harvest maturity (Table 3) shows that the time of sampling did not bias the firmness results. Now that the use of the Instron for detecting differences in firmness has been established, the issue of determination of optimum harvest maturity can be addressed in future studies.

The correlations between puncture force and the other fruit characteristics were either not significant or below 0.35, indicating that indirect selection for firmness would not be feasible. The correlation coefficient of 0.49 between flesh and total puncture force values suggests that a high total puncture force does not ensure that flesh values will also be high (Table 3).

TABLE 3

Correlation Coefficients Between Fruit Characteristics Across 29 Genotypes of Sweet Cherry

| | Flesh | Total | SSC | FRF | Wt | Diam |
|---|---|---|---|---|---|---|
| Flesh | — | | | | | |
| Total | 0.49** | — | | | | |
| SSC | NS | 0.20** | — | | | |
| FRF | NS | NS | −0.32** | — | | |
| Weight | 0.22** | NS | NS | NS | — | |
| Diameter | 0.32** | 0.23** | 0.22** | NS | 0.96** | — |

NS/**Nonsignificant or significant at the 1% level, respectively.

The total firmness force value is not only an indication of skin strength, but is influenced by the firmness of the underlying flesh, so that the value obtained is a mixture of the two components. Therefore, when the percentage of flesh firmness to total firmness is calculated the values are surprisingly low, ranging from 15% to 34%. This does not suggest that the skin alone is responsible for the remaining percentage, but rather that it is the interaction of the skin and flesh.

When cultivars of similar total firmness are compared, the differences is flesh firmness can be large. This is found throughout the range of total firmness values as evidenced by the three pairs shown. The difference in the magnitude of flesh vs. total firmness has important implications in choosing cultivars for use in genetic improvement. A genotype with high flesh and high total values is preferred. Where genotypes have a high total value with a low flesh value, it is primarily the skin that is responsible for the perceived firmness. The strong contribution of skin to total firmness is evident in the case of NY 1507 and 'Victor' where the flesh accounts for only 17% and 15% of the total firmness, respectively. To emphasize the importance of flesh firmness to the perception of total firmness, 'Van' is regarded as being firm, yet in total firmness it ranks very low. However, the flesh is very firm and accounts for a relatively high percentage (26%) of the total value. The flesh texture of 'Van' may be responsible for it reputation for firmness.

Examination of Table 1 reveals that many commercial cultivars share a common parentage, with 'Napoleon' found several times in the pedigree of the firmer selections (Tables 1 and 2). The firmness values of several New York selections are higher than the commercial cultivars used in their development. Several New York selections are as firm as the commercially important 'Bing' in both total and flesh firmness with NY 6476 being firmer than 'Bing' in both categories.

Use of the Instron not only allows us to identify those sources of firmness to be used in breeding, but also enable us to evaluate the progeny for both components of firmness. Studies of progenies resulting from hybridizations between the firmest cultivars and selections will provide greater understanding of the inheritance of firmness. This may aid the improvement in fruit firmness, which should greatly extend the storage life of the sweet cherry and result in improved fruit quality in the marketplace.

Figure 1:
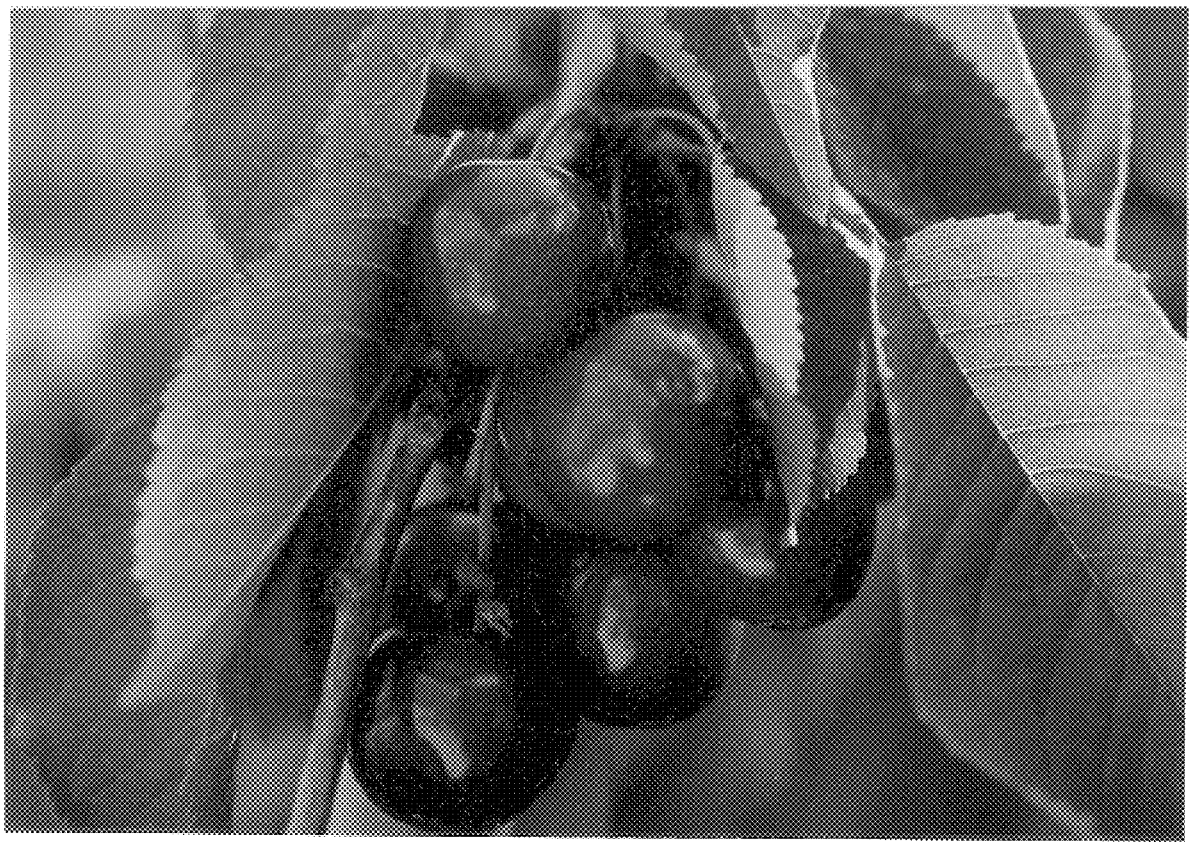
FIG. 1 shows fruit clustering of 'Hartland'.

The numerical color designations set forth herein are taken from The Royal Horticultural Society Colour Chart (1976).

DESCRIPTION OF THE INVENTION

This invention relates to a new and distinct cultivar of the cherry tree, 'Hartland', which we discovered in a test planting belonging to the New York Agricultural Experiment Station, Cornell University, Geneva, Ontario County, N.Y. This discovery is a product of a cherry breeding research program of the New York State Agricultural Experiment Station (Station). Asexual reproduction of the tree has been performed by the inventors in Geneva, N.Y.

Pollination: We have conducted experiments to determine the pollination biology specifics about 'Hartland'. Our experiments took the form of field tests to cover the opening flowers with paper bags and thereby isolate flowers of 'Hartland' from bee visitation. Such bagging allowed us to subsequently apply pollen derived from known sources to the flower stigmas to determine the specific pollination compatibility group to which 'Hartland' belongs. It is self unfruitful and belongs to Group VI as described by Crane and Brown, 1955. "Incompatibility and varietal confusion in cherries" Sci. Hort., 11, pp.53–55. This pollination group is infrequent in its representation amongst other commercial sweet cherry cultivars. 'Hartland''s flowers contain ample amounts of viable pollen which is available for cross pollination via insect vectors when the flowers open midway through the blooming time of sweet cherries in Geneva. Hence, 'Hartland' is a highly useful pollenizer for other self unfruitful cultivars.

Electrophoretic enzyme tests: We conducted electrophoretic enzyme tests in 1990 to determine the presence or absence of certain specific enzymes. 'Hartland' is positive for diaphorase (heterozygous), glucose phosphate isomerase (homozygous), aconitase (heterozygous), and 6-glucose phosphogluconate dehydrogenase (homozygous). While other cherry cultivars or genotypes may have these same characteristics we are only aware that Windsor, 'Hartland''s maternal parent, has the same isozyme pattern for these enzymes.

Flowers and flowering: Flowers are born on lateral buds of spurs on branches which are two years old or older. They also are born from axillary buds of shoots laid down the previous growing season. Typically, 3 to 5 flowers are produced from spur buds and 3 to 5 flowers are also borne on proximal region axillary buds on the previous season's shoots. Timing of flower emergence is mid-season at about the same time as 'Bing' and 'Van' and occurs in Geneva, N.Y. on about May 5.

Flowers are white, single and have no unusual features that distinguish them from those of other sweet cherry cultivars. They are structurally typical of *Prunus avium* with a base number of five petals and about 25 stamens. Pedicels are about 2 cm long and of intermediate thickness, about 1.0 mm. Anthers are yellow and pollen is yellow-orange. Self pollinations of 'Hartland' are unfruitful.

Fruiting habit and fruit: 'Hartland' trees which are grafted to the common cherry rootstock, 'Mazzard Seedling' (Mazzard), typically have flowers appear after only two growing seasons on trees that have been planted in their orchard position. Fruit is often set on trees which flower for the first time. This high precociousness to bear flowers and set fruit is a distinguishing feature of 'Hartland' when it is grafted to Mazzard.

The individual fruits of 'Hartland' are round-slightly oblong, their skin color at maturity is greyed-purple 187B. Their flesh color is a slightly lighter shade of greyed-purple, 185A. Fruits are cordate in shape, symmetrical, and medium in size compared to most other sweet cherry cultivars. They are about 2.0 to 2.8 cm in diameter of width and 2.1 to 3.0 cm in length (stem end to pistillate end). Pits are medium, 80 mm long by 60 mm wide across the suture and round to round-conic with slightly protruding tip on stigmatic end. The pit shape is cordate with a distinct raised stem-end protrusion at the top of the shallowly grooved suture. Flesh adherence to the pit is not freestone, but degree of adherence is difficult to judge in cherries, as compared to other stone fruit crops which have larger stones and more distinct abscission of their flesh from their stones. Fruits of 'Hartland' resist moisture stress induced cracking better than the Bing cultivar. The soluble solids level of 'Hartland' fruit in Geneva usually exceeds 14 percent. This is a lower value than most other commercially utilized cultivars of sweet cherry. This is of questionable commercial merit but is a distinguishing feature of the invention. Fruits have a rich cherry flavor. They are medium in firmness, about 0.77 Instron units at maturity. They have a fruit removal force at maturity of about 489 grams of pull force. Fruit ripening is about with the Bing and Schmidt cultivars, which is about 50 days after full bloom in Geneva. Timing of fruit ripening in Geneva, N.Y. occurs about June 26–28.

Tree habit: 'Hartland''s tree habit is moderately vigorous, very spreading with many lateral branches produced along the apical portions of about 25% of the previous season's growth. This tree habit and branching structure leads to a round, slightly drooping form of growth in mature fruiting trees.

Shoots: 'Hartland''s shoots are of medium length with many lateral branches. They have small lenticels. In the autumn after cessation of terminal growth extension, the color of the bark at the fourth internode above the proximal position is greyed-brown 200D on the side of the stem which is commonly exposed to direct sunlight. The other side of the stem is greyed-brown 199B. The sun exposed color contrasts to greyed-orange 165B in the Bing cultivar.

Bark: At Geneva, N.Y., the color of the bark on the north side of the trunks of mature, fruiting trees at 50 cm above the soil line is Greyed-Purple Group 183A while 'Bing' cultivar is much darker, Greyed-Purple 187A. 'Hartland' has elliptical lenticels that are grey in color and have an orangish line or crack in their center. Such lenticels are usually wider and two to three times longer (often 2 to 3 cm) than those on the 'Bing' cultivar (usually about 1 and 1½ cm), and on 'Hartland', they often form a chain that is continuous around a high percentage of the circumference of the trunk, whereas in 'Bing', they are discontinuous and less frequent, so that much more smooth bark is present on the lower trunk of 'Bing' than on 'Hartland'.

Figure 2:
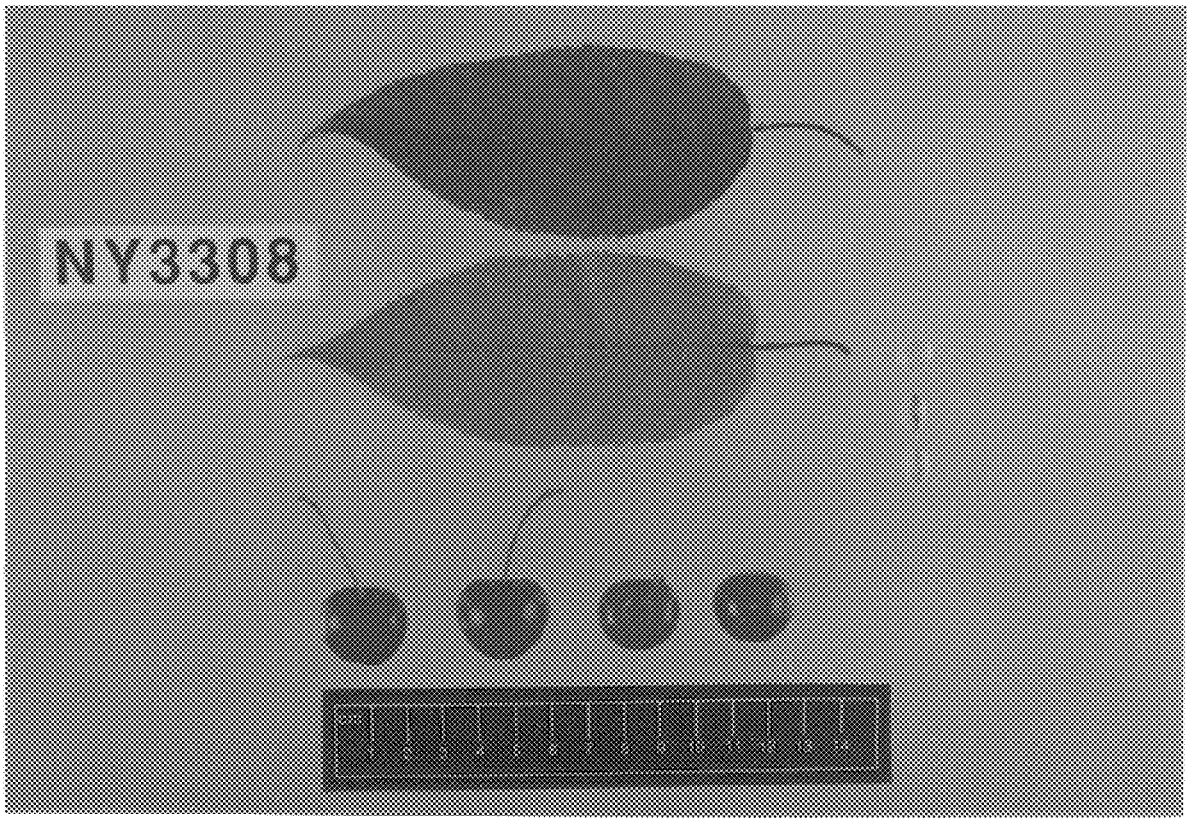
FIG. 2 shows, at scale, the fruit, pits and the front and back view of two 'Hartland' leaves.

Leaves: Leaves of 'Hartland' are medium in leaf area, usually symmetrical, lamella glabrous and smooth with adaxial lamella surface dark green 139A, abaxial surface yellow-green 148B, and margins coarsely serrate with 2 to 2.5 serrations per cm, glands round and numerous, 3 to 5 per leaf, stipules are present during early stages of growth but abscise before fruit maturity, petioles 4 to 4.5 cm long, leaf poise typically 45 to 50 degrees from the shoot, leaves fold upward at the mid-vein during heat stress. The red mid-vein coloration shown in FIG. 2 is not so unique and distinctive as to be used as an identification criterion. Although red mid-vein coloration is present in modest amount on some leaves, no pattern could be determined that distinguished 'Hartland' from the many other cultivars that have similar coloration on their leaves.

Usefulness

'Hartland' sweet cherry is well suited for production to fulfill certain processed and fresh market demands in most eastern USA and eastern Canadian cherry orchard businesses. Such orchard sites are characterized by their frequent spring frosts during sweet cherry blossom seasons and there are many seasons when near freezing temperatures persist during much of the blossom period. Hence, a pollenizer cultivar is needed which has mid-bloom time anthesis, annual return of heavy flowering, ample pollen availability, and which is genetically compatible with most other commercial cultivars. 'Hartland' meets these criteria and has a heavy cropping pattern and a favorable season of fruit ripening. It has adequate quality to meet most market needs. In our field observations of resistance to bacterial canker we have noted better resistance in 'Hartland' than in many cultivars we have tested. This combination of favorable traits should result in 'Hartland' being well received by orchardists as a new early mid-season, pollenizer, dual purpose cherry with fruit being acceptable for most market uses.

What we claim is:

1. A new and distinct sweet cherry cultivar as herein described and illustrated.

* * * * *